United States Patent [19]

Berg

[11] Patent Number: 4,969,977
[45] Date of Patent: * Nov. 13, 1990

[54] SEPARATION OF 2-METHYL-BUTANOL-1 FROM PENTANOL-1 BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[ * ] Notice: The portion of the term of this patent subsequent to Dec. 1, 2004 has been disclaimed.

[21] Appl. No.: 302,980

[22] Filed: Jan. 30, 1989

[51] Int. Cl.$^5$ .................... B01D 3/40; C07C 29/84
[52] U.S. Cl. .......................... 203/51; 203/60; 203/61; 203/65; 568/913
[58] Field of Search .................. 203/51, 61, 60, 65, 203/63; 568/913, 918

[56] References Cited

U.S. PATENT DOCUMENTS

| | | | |
|---|---|---|---|
| 2,551,584 | 5/1951 | Carlson et al. | 203/53 |
| 2,575,243 | 11/1951 | Carlson et al. | 203/60 |
| 2,595,805 | 5/1952 | Morrell et al. | 203/84 |
| 4,710,274 | 12/1987 | Berg et al. | 203/51 |
| 4,710,275 | 12/1987 | Berg et al. | 203/51 |
| 4,715,933 | 12/1987 | Berg et al. | 203/51 |
| 4,732,653 | 3/1988 | Berg et al. | 203/51 |
| 4,756,803 | 7/1988 | Berg et al. | 203/51 |

*Primary Examiner*—Wilbur Bascomb

[57] ABSTRACT

2-Methyl butanol-1 cannot be completely removed from 2-methyl butanol-1-pentanol-1 mixtures by distillation because of the proximity of their boiling points. 2-methyl butanol-1 can be readily removed from mixtures of these alcohols by using extractive distillation in which the extractive agent is a mixture of aromatic carboxylic acids or aromatic carboxylic esters. Typical examples of effective agents are: benzoic acid, ethyl salicylate and salicylic acid; methyl benzoate, methyl p-hydroxy benzoate and phenyl salicylate.

5 Claims, No Drawings

SEPARATION OF 2-METHYL-BUTANOL-1 FROM PENTANOL-1 BY EXTRACTIVE DISTILLATION

This application is related to Application No. 07/087,811 filed Aug. 22, 1986, abandoned.

FIELD OF THE INVENTION.

This invention relates to a method for separating 2-methyl butanol-1 from pentanol-1 using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

2-Methyl and pentanol-1 are two of the widely used alcohols in commerce today. When they are used as solvents, they frequently end up as a mixture of solvents. Whenever practical, it is mandatory to recover the solvent and re-use it.

2-Methyl butanol-1 boils at 128° C., pentanol-1 at 138° C. and these two have a relative volatility of 1.4, making it difficult to separate these two by rectification. Extractive distillation would be an attractive method of effecting the separation of 2-methyl butanol-1 from pentanol-1 if agents can be found that (1) will alter the relative volatility between 2-methyl butanol-1 and pentanol-1, (2) form no azeotropes with 2-methyl butanol-1 or pentanol-1 and (3) are easy to recover from pentanol-1, that is boil sufficiently above pentanol-1 to make the separation by rectification possible with only a few theoretical plates.

Extractive distillation typically requires the addition of an equal amount to twice as much extractive agent as the on each plate of the rectification column. The extractive agent should be heated to about the same temperature as the plate into which it is introduced. Thus extractive distillation imposes an additional heat requirement on the column as well as somewhat larger plates. However, this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the isopropanol otherwise it will form a two phase azeotrope with it and some other method of separation will have to be employed.

TABLE 1

Effect of Relative Volatility on the Separation of 2-Methyl butanol-1 From pentanol-1 at 95% Purity

| Relative Volatility | Theoretical Plates | Actual Plates, 75% Efficiency | Actual Plates, 75% Eff., Min. Reflux |
|---|---|---|---|
| 1.4 | 66 | 88 | 114 |
| 1.5 | 50 | 67 | 87 |
| 1.6 | 40 | 53 | 69 |
| 1.65 | 35 | 47 | 61 |
| 1.7 | 32 | 43 | 55 |

The advantage of employing an effective extractive distillation agent for this separation is shown in Table 1. When ordinary rectification is used, 114 actual plates of 75% efficiency are required at minimum reflux ratio to separate 2-methyl butanol-1 from pentanol-1 in 95% purity. If extractive distillation is employed with an agent that converts the relative volatility to 1.7, only 55 actual plates are required.

A number of investigators have reported the separation of lower boiling alcohols, one from another, by extractive distillation. Carlson, U.S. Pat. No. 2,570,205 used sulfolane to separate n-propanol from butyl alcohols. from isobutanol. They remained in the same fraction. Drout, U.S. Pat. No. 2,552,412 used ethylene glycol, 1,3-propanediol and diethylene glycol as the agents in separating a mixture containing ethanol, sec. butanol, sec. amyl alcohol and t-amyl alcohols. Smith, U.S. Pat. No. 2,559,519 used glycol ethers to separate alcohol mixtures containing ethanol, propanol, glycol and 1,3-butylene glycol as the extractive agent to separate n-propanol from sec. butanol. Carlson, U.S. Pat. No. 2,575,243 used glycol Morrell, U.S. Pat. No. 2,591,712 used paraffinic, naphthenic or aromatic hydrocarbon oils to separate close boiling anhydrous alcohols. Morrell, U.S. Pat. No. 2,591,713 used water and a white oil to separate the lower alcohols. Morrell, U.S. Pat. No. 2,706,707 used aqueous solutions ofsodium xylene sulfonate or sodium p-cymene sulfonate in teh separation of lower alcohols.

OBJECTIVE OF THE INVENTION

The object of this invention is to provide a process or method of extractive distillation that will enhance the relative volatility of 2-methyl butanol-1 from pentanol-1 in their separation in a rectification column. It is a further objective of this invention to identify organic compounds which are stable, can be separated from 2-butanol by rectification with relatively few plates and can be recycled to the extractive distillation column and re-used with little decomposition.

SUMMARY OF THE INVENTION

The objects of this invention are provided by a process for separating 2-methyl butanol-1 from pentanol-1 which entails the use of certain organic compounds as the agent in extractive distillation.

DETAILED DESCRIPTION OF THE INVENTION

I have discovered that benzoates and salicylates will effectively enhance the relative volatility between 2-methyl-butanol-1 and pentanol-1 and permit the separation of pure 2-methyl-butanol-1 from pentanol-1 by rectification when employed as the agents in extractive distillation. Table 2 lists benzoic acid, its mixtures and the approximate proportions that I have found to be effective. Table 3 lists salicyclic acid and its mixtures that are effective. Table 4 lists methyl benzoate and its mixtures; Table 5 lists salicylates that are effective. The data in Tables 2, 3, 4 and 5 were obtained in a vapor-liquids equilibrium still. In most cases, the starting material was a 50—50% 2-methyl-butanol-1 - pentanol-1 mixture. The ratios are the parts of extractive agents used per part of 2-methyl-butanol-1-pentanol-1 mixture. The relative volatilities are listed for each of two ratios employed.

TABLE 2

Extractive Distillation Agents Containing Benzoic Acid

| Compounds | Ratios | | Relative Volatilities | |
|---|---|---|---|---|
| Benzoic acid, Ethyl salicylate | $(1/2)^2$ | $(3/5)^2$ | 1.49 | 1.52 |
| Benzoic acid, Methyl benzoate | " | " | 1.59 | 1.40 |
| Benzoic acid, Methyl p-hydroxy benzoate | " | " | 1.59 | 1.47 |
| Benzoic acid, Salicylic acid, Ethyl salicylate | $(1/3)^3$ | $(2/5)^3$ | 1.55 | 1.49 |
| Benzoic acid, Salicylic acid, Methyl benzoate | " | " | 1.58 | 1.54 |
| None | — | — | 1.40 | |

TABLE 3

Extractive Distillation Agents Containing Salicylic Acid

| Compounds | Ratios | | Relative Volatilities | |
|---|---|---|---|---|
| Salicylic acid | 1 | | 1.59 | |
| Salicylic acid, Butyl p-hydroxybenzoate | $(1/2)^2$ | $(3/5)^2$ | 1.49 | 1.58 |
| Salicylic acid, Methyl p-hydroxybenzoate | " | " | 1.62 | 1.56 |
| Salicylic acid, Methyl tetrahydro phthalic anhydride | " | " | 1.66 | 1.50 |
| Salicylic acid, Phenyl salicylate | " | " | 1.58 | 1.67 |
| Salicylic acid, Phthalic anhydride | " | " | 1.57 | 1.47 |
| Salicylic acid, Butyl p-hydroxybenzoate, Ethyl salicylate | $(1/3)^3$ | $(2/5)^3$ | 1.55 | 1.55 |
| Salicylic acid, Methyl p-hydroxybenzoate, Ethyl salicylate | " | " | 1.60 | 1.76 |
| Salicylic acid, Methyl p-hydroxybenzoate, Trimellitic anhydride | " | " | 1.67 | 1.45 |
| Salicylic acid, Methyl p-hydroxybenzoate, Methyl benzoate | " | " | 1.64 | 1.50 |
| Salicylic acid, Methyl tetrahydro phthalic anhydride, Methyl benzoate | " | | 1.52 | |
| Salicylic acid, Phenyl salicylate, Methyl benzoate | " | " | 1.54 | 1.48 |

TABLE 4

Extractive Distillation Agents Containing Methyl Benzoate

| Compounds | Ratios | | Relative Volatilities | |
|---|---|---|---|---|
| Methyl benzoate (MeBn) | 1 | | 1.56 | |
| MeBn, Methyl p-hydroxybenzoate | $(1/2)^2$ | $(3/5)^2$ | 1.63 | 1.50 |
| MeBn, Phenyl salicylate | " | " | 1.61 | — |
| MeBn, Phthalic anhydride | " | " | 1.77 | 1.56 |
| MeBn, Phthalic anhydride, Methyl salicylate | $(1/3)^3$ | $(2/5)^3$ | 1.52 | 1.89 |
| MeBn, Phthalic anhydride, Maleic anhydride | " | " | 1.61 | 1.47 |
| MeBn, Methyl p-hydroxbenzoate, Phenyl salicylate | " | " | 1.58 | 1.52 |
| MeBn, Methyl p-hydroxbenzoate, Trimellitic anhydride | " | " | 1.52 | |

TABLE 5

Extractive Distillation Agents Containing Salicylates

| Compounds | Ratios | | Relative Volatilities | |
|---|---|---|---|---|
| Methyl salicylate | 1 | 6/5 | 1.51 | 1.47 |
| Methyl salicylate, Phthalic anhydride | $(1/2)^2$ | $(3/5)^2$ | 1.63 | 1.61 |
| Methyl salicylate, Phenyl salicylate, Benzyl p-hydroxybenzoate | $(1/3)^3$ | $(2/5)^3$ | 1.51 | 1.55 |
| Ethyl salicylate | 1 | 6/5 | 1.65 | 1.52 |
| Ethyl salicylate, Salicylic acid, Trimellitic anhydride | $(1/3)^3$ | $(2/5)^3$ | 1.51 | 1.73 |
| Phenyl salicylate | 1 | | 1.56 | |

TABLE 6

Data From Run Made In Rectification Column On 2-Methyl-butanol-1-Pentanol-

| Agent | Time Hrs. | Stillpot Temp. °C. At Start | Stillpot Temp. °C. Sampling | Overhead Temp. When Sampling | Wt % 2-Me-BuOH-1 Overhead | Wt % 2-Me-BuOH-1 Bottoms | Relative Volatility |
|---|---|---|---|---|---|---|---|
| None | 6 | | 133 | 122 | 59 | 24 | 1.4 |
| 50% MeSal-50% PhAn | 1 | 133 | 151 | 121 | 64 | 20 | 1.54 |
| 50% MeSal-50% PhAn | 2 | 133 | 169 | 121 | 66 | 19 | 1.60 |
| 50% MeSal-50% PhAn | 3 | 133 | 177 | 121 | 66 | 18.5 | 1.62 |

Notes:
MeSal = Methyl salicylate, PhAn = Phthalic anhydride; Agent feed rate was 20 ml/m
Agent temp. was 85° C., Boilup rate was 10–20 ml/min.

The compounds which are effective when used alone are methyl benzoate, methyl salicylate, ethyl salicylate, phenyl salicylate and salicylic acid. The compounds which are effective when used in mixtures of two or more components are methyl p-hydroxybenzoate, butyl p-hydroxy-benzoate, phthalic anhydride, benzyl p-hydroxybenzoate, methyl tetrahydro phthalic anhydride, maleic anhydride and trimellitic anhydride.

The two relative volatilities listed correspond to the two different ratios investigated. For example, in Table 5, one part of ethyl salicylate with one part of the 2-methyl-butanol-1-pentanol-1 mixture gives a relative volatility of 1.65, 6/5 parts of ethyl salicylate give 1.52. One half part of methyl salicylate with one half part of phthalic anhydride with one part of 2-methyl-butanol-1-pentanol-1 mixture gives a relative volatility of 1.63, 3/5 parts of methyl salicylate plus 3/5 parts of phthalic anhydride give 1.61. One third parts of ethyl salicylate plus ⅓ parts of salicylic acid plus ⅓ parts of trimellitic anhydride mixed with one part of 2-methyl-butanol-1-pentanol-1 mixture give a relative volatility of 1.51, with 2/5 parts, these three give 1.73. In every example in Tables 2, 3, 4 and 5, the starting material is a 50–50% mixture of 2-methyl-butanol-1-pentanol-1 which possesses a relative volatility of 1.4.

A 50% methyl salicylate-50% phthalic anhydride mixture was then evaluated as an extractive rectification agent in a glass perforated plate rectification column possessing 4.5 theoretical plates. The results are listed in Table 6. The 2-methyl-butanol-1-pentanol-1 mixture used contained 50% 2-methyl-butanol-1. The first run is with no extractive agent and with 220 grams in the stillpot. After six hours of operation, the separation is that in accordance with a relative volatility of 1.4. The second run is with methyl salicylate-phthalic anhydride as the extractive agent. After one hour of continuous operation, the relative volatility was 1.54, after two hours, 1.60 and after three hours, 1.62. Experience with this column has shown that three hours of steady operation are required to reach equilibrium. The relative volatility attained, 1.62, can be compared with the 1.63 obtained for methyl salicylate-phthalic anhydride with the vaporliquid equilibrium still listed in Table 5.

THE USEFULNESS OF THE INVENTION.

The usefulness or utility of this invention can be demonstrated by referring to the data presented in Tables 1, 2, 3, 4, 5 & 6. all of the successful extractive distillation agents show that 2-methyl-butanol-1 can be removed from pentanol-1 by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity 2-methyl-butanol-1 from any mixture with pentanol-1. The stability of the compounds used and the boiling point difference is such that complete recovery and recycle is obtainable by a simple distillation and the amount required for make-up is small.

WORKING EXAMPLES

1. Fifteen grams of 2-methyl-butanol-1 (2-MeBuOH), 55 grams of pentanol-1 (PeOH-1) and fifty grams of methyl salicylate were charged to an Othmer type glass vapor-liquid equilbrium still and refluxed for five hours. Analysis of the vapor and liquid by gas chomatography gave a vapor composition of 29.6% 2-MeBuOH, 70.4% PeOH-1; a liquid composition of 20.3% 2-MeBuOH, 79.7% PeOH-1. This indicates a relative volatility of 1.65. Ten grams of ethyl salicylate were added and refluxing continued for another six hours. Analysis indicated a vapor composition of 30.5% 2-MeBuOH, 69.5% PeOH-1; a liquid composition of 22.5% 2-MeBuOH, 77.5% PeOH-1 which is a relative volatility of 1.52.

EXAMPLE 2

Thirty-five grams of 2-MeBuOH, 35 grams of PeOH-1, 25 grams of methyl salicylate and 25 grams of phthalic anhydride were charged to the vapor-liquid equilibrium still and refluxed for 11 hours. Analysis indicated a vapor composition of 57.1% 2-MeBuOH, 42.9% PeOH-1; a liquid of 1.63. Five grams of methyl salicylate and five grams of phthalic anhydride were added and refluxing continued for another 11 hours. Analysis indicated a vapor composition of 52.2% 2-MeBuOH, 47.8% PeOH-1; a liquid composition of 40.4% 2-MeBuOH, 59.6% PeOH-1 which is a relative volatility of 1.61.

EXAMPLE 3

Twenty grams of 2-MeBuOH, fifty grams of PeOH-1, 17 grams of ethyl salicylate, 17 grams of salicylic acid and 17 grams of trimellitic anhydride were charged to the vapor-liquid equilibrium still and refluxed for five hours. Analysis indicated a vapor composition of 37.4% 2-MeBuOH, 62.6% PeOH-1; a liquid composition of 28.4% 2-MeBuOH, 71.6% PeOH-1 which is a relative volatility of 1.51. Three grams each of ethyl salicylate, salicylic acid and trimellitic anhydride were added and refluxing continued for another seven hours. Analysis indicated a vapor composition of 39.2% 2-MeBuOH, 60.8% PeOH-1 and a liquid composition of 27.1% 2-MeBuOH, 72.9% PeOH-1 which is a relative volatility of 1.73.

EXAMPLE 4

A glass perforated plate rectification column was calibrated with ethylbenzene and p-xylene which possesses a relative volatility of 1.06 and found to have 4.5 theoretical plates. A solution of 110 grams of 2-MeBuOH and 110 grams of PeOH-1 was placed in the stillpot and heated. The column was operated at total reflux for six hours to establish equilibrium throughout. Overhead and bottoms samples of approximately 2 ml. were collected analysed by gas chromatography. The overhead analysis was 59% 2-MeBuOH, 41% PeOH-1 and the stillpot analysis was 24% 2-MeBuOH and 76% PeOH-1. Using these compositions in the Fenske equation with the number of theoretical plates in the column being 4.5, gave an average relative volatility of 1.4 for each theoretical plate. An extractive agent consisting of 50% methyl salicylate, 50% phthalic anhydride was pumped into the column at a rate of 20 ml/min. The temperature of the extractive agent as it entered the column was 85° C. After establishing the feed rate of the extractive agent, the heat input to the 2-MeBuOH-PeOH-1 in the stillpot was adjusted to give a reflux rate of 10-20 ml/min. After one hour of operation, overhead and bottoms samples were collected and analysed. The overhead analysis was 64% 2-MeBuOH, 36% PeOH-1 and the bottoms analysis was 20% 2-MeBuOH, 80% PeOH-1 which gave an average relative volatility of 1.54 for each theoretical plate. After two hours of total operating time, the overhead and bottoms samples were again taken and analysed. The overhead composition was 66% 2-MeBuOH, 34% PeOH-1 and the bottoms composition was 19% 2-MeBuOH, 81% PeOH-1. This gave an average relative volatility of 1.60 for each theoretical plate. After three hours of total operating time, the overhead and bottoms samples were again taken and analysed. The overhead composition was 66% 2-MeBuOH, 34% PeOH-1 and the bottoms composition was 18.5% 2-MeBuOH, 81.5% PeOH-1. This gave an average relative volatility of 1.62 for each theoretical plate. The data in this example is summarized in Tables 6.

I claim:

1. A method for recovering 2-methyl-butanol-1 from a mixture of 2-methyl-butanol-1 and pentanol-1 which comprises distilling a mixture of 2-methyl-butanol-1 and pentanol-1 in a rectification column in the presence of about one part of extractive agent per part of 2-methyl-butanol-1-pentanol-1 mixture, recovering the 2-methyl-butanol-1 as overhead product and obtaining the extractive agent and pentanol-1 from the stillpot, the extractive agent comprises a mixture of benzoic acid, ethyl salicylate, and salicylic acid.

2. A method for recovering 2-methyl-butanol-1 from a mixture of 2-methyl-butanol-1 and pentanol-1 which comprises distilling a mixture of 2-methyl-butanol-1 and pentanol-1 in a rectification column in the presence of about one part of extractive agent per part of 2-methyl-butanol-1-pentanol-1 mixture, recovering the 2-methyl-butanol-1 as overhead product and obtaining the extractive agent and pentanol-1 from the still port, the extractive agent comprises salicylic acid and at least two materials selected from the group consisting of methyl benzoate, phenyl salicylate and methyl p-hydroxybenzoate.

3. A method for recovering 2-methyl-butanol-1 from a mixture of 2-methyl-butanol-1 and pentanol-1 which comprises distilling a mixture of 2-methyl-butanol-1 and pentanol-1 in a rectification column in the presence of about one part of extractive agent per part of 2-methyl-butanol-1-pentanol-1 mixture, recovering the 2-methyl-butanol-1 as overhead product and obtaining the extractive agent and pentanol-1 from the stillpot, the extractive agent comprises methyl benzoate and at least two materials selected from the group consisting of methyl salicylate, phenyl alicylate, methyl p-hydroxybenzoate and maleic anhydride.

4. A method for recovering 2-methyl-butanol-1 from a mixture of 2-methyl-butanol-1 and pentanol-1 which comprises distilling a mixture of 2-methyl-butanol-1 and pentanol-1 in a rectification column in the presence of about part of extractive agent per part of 2-methyl-butanol-1-pentanol-1 mixture, recovering the 2-methyl-butanol-1 as overhead product and obtaining the extractive agent and pentanol-1 from the stillpot, the extractive agent comprises a mixture of methyl salicylate, phenyl salicylate, and benzyl p-hydroxybenzoate.

5. A method for recovering 2-methyl-butanol-1 from a mixture of 2-methyl-butanol-1 and pentanol-1 which comprises distilling a mixture of 2-methyl-butanol-1 and pentanol-1 in a rectification column in the presence of about one part of extractive agent per part of 2-methyl-butanol-1-pentanol-1 mixture, recovering the 2-methyl-butanol-1 as overhead product and obtaining the extractive agent and pentanol-1 from the stillpot, the extractive agent comprises a mixture of ethyl salicylate, salicylic acid and trimellitic anhydride.

* * * * *